(12) United States Patent
Refael

(10) Patent No.: US 7,869,856 B2
(45) Date of Patent: Jan. 11, 2011

(54) ENCAPSULATED MEDICAL IMAGING DEVICE AND METHOD

(75) Inventor: Moshe Refael, 83 Eitanim St., Nofit (IL) 36001

(73) Assignees: Moshe Refael, Nofit (IL); Avi Goldsobel, Tel Aviv (IL); Engel Research & Development (1993) Ltd., Tel Aviv (IL); L.Z. Ashlang Finance Ltd., Haifa (IL)

( * ) Notice: Subject to any disclaimer, the term of this patent is extended or adjusted under 35 U.S.C. 154(b) by 936 days.

(21) Appl. No.: 10/169,615

(22) PCT Filed: Jan. 10, 2001

(86) PCT No.: PCT/IL01/00020

§ 371 (c)(1),
(2), (4) Date: Jan. 9, 2003

(87) PCT Pub. No.: WO01/50941

PCT Pub. Date: Jul. 19, 2001

(65) Prior Publication Data

US 2003/0208107 A1    Nov. 6, 2003

(30) Foreign Application Priority Data

Jan. 13, 2000    (IL) .................................... 134017

(51) Int. Cl.
*A61B 5/00*    (2006.01)
(52) U.S. Cl. ...................... 600/407; 600/160
(58) Field of Classification Search .......... 600/160, 600/167–181, 424, 476, 407
See application file for complete search history.

(56) References Cited

U.S. PATENT DOCUMENTS

| 3,643,653 | A |   | 2/1972  | Takahashi et al. |
|-----------|---|---|---------|------------------|
| 3,889,662 | A |   | 6/1975  | Mitsui |
| 3,918,438 | A |   | 11/1975 | Hayamizu et al. |
| 4,278,077 | A |   | 7/1981  | Mizumoto |
| 4,573,450 | A |   | 3/1986  | Arakawa |
| 4,803,992 | A |   | 2/1989  | Lemelson |
| 4,846,154 | A |   | 7/1989  | MacAnally et al. |
| 5,166,787 | A |   | 11/1992 | Irion |
| 5,430,475 | A | * | 7/1995  | Goto et al. ................... 348/65 |
| 5,547,455 | A |   | 8/1996  | McKenna et al. |
| 5,602,531 | A |   | 2/1997  | Rude et al. |
| 5,604,531 | A |   | 2/1997  | Iddan et al. |
| 5,653,677 | A |   | 8/1997  | Okada et al. |
| 5,662,587 | A |   | 9/1997  | Grundfest et al. |
| 5,681,260 | A |   | 10/1997 | Ueda et al. |
| 5,800,341 | A |   | 9/1998  | McKenna et al. |
| 5,833,603 | A | * | 11/1998 | Kovacs et al. ............... 600/317 |
| 5,993,378 | A | * | 11/1999 | Lemelson ................... 600/109 |

(Continued)

FOREIGN PATENT DOCUMENTS

DE    3440177 A1    11/1984

(Continued)

*Primary Examiner*—Brian Casler
*Assistant Examiner*—Jonathan G Cwern
(74) *Attorney, Agent, or Firm*—William H. Dippert; Eckert Seamans Cherin & Mellott, LLC

(57) ABSTRACT

The present invention relates to an encapsulated medical imaging device (1) and method for imaging the gastrointestinal tract in patients using optical scanning technologies.

51 Claims, 7 Drawing Sheets

U.S. PATENT DOCUMENTS

| | | | |
|---|---|---|---|
| 6,240,312 B1 * | 5/2001 | Alfano et al. | 600/476 |
| 6,402,686 B1 | 6/2002 | Ouchi | |
| 6,984,205 B2 * | 1/2006 | Gazdzinski | 600/160 |
| 2001/0017649 A1 | 8/2001 | Yarm | |
| 2003/0029558 A1 | 2/2003 | Hochrainer | |

FOREIGN PATENT DOCUMENTS

| | | | |
|---|---|---|---|
| JP | 64-76822 | | 3/1989 |
| JP | HEI-3-9705 | | 1/1991 |
| JP | 3159629 | | 7/1991 |
| JP | 4144533 | | 5/1992 |
| JP | 05-015515 | * | 1/1993 |
| JP | 7111985 | | 5/1995 |
| JP | 8-248326 | | 9/1996 |
| WO | WO 98/11816 | | 3/1998 |
| WO | WO 00/22975 | * | 4/2000 |

* cited by examiner

Fig. 1a
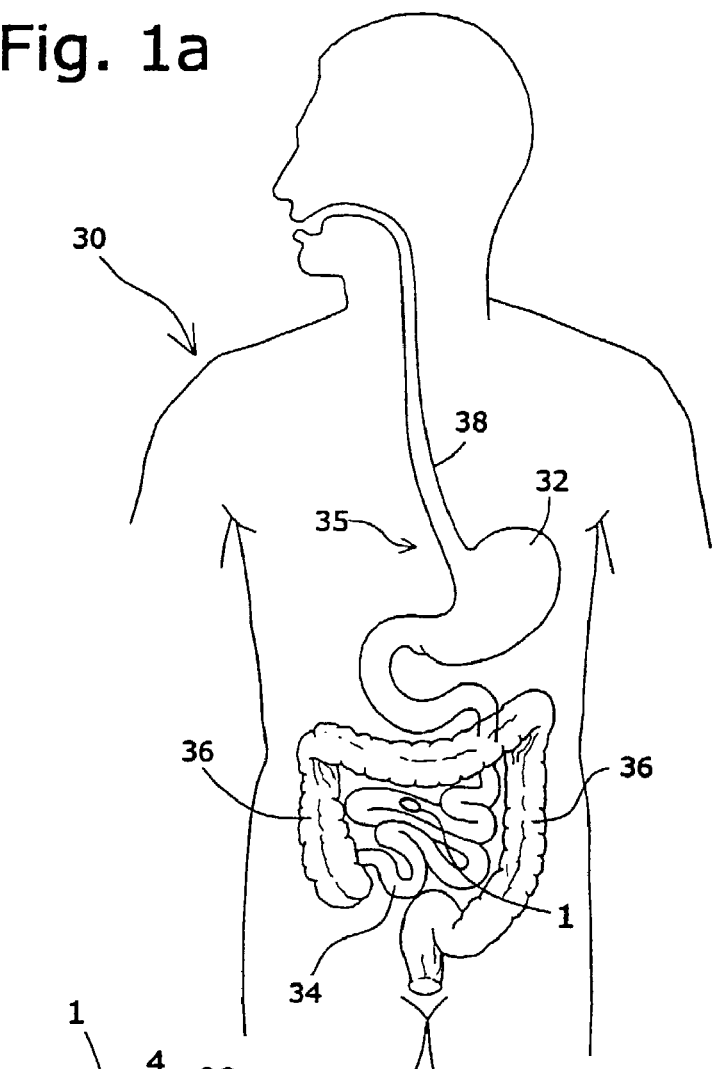
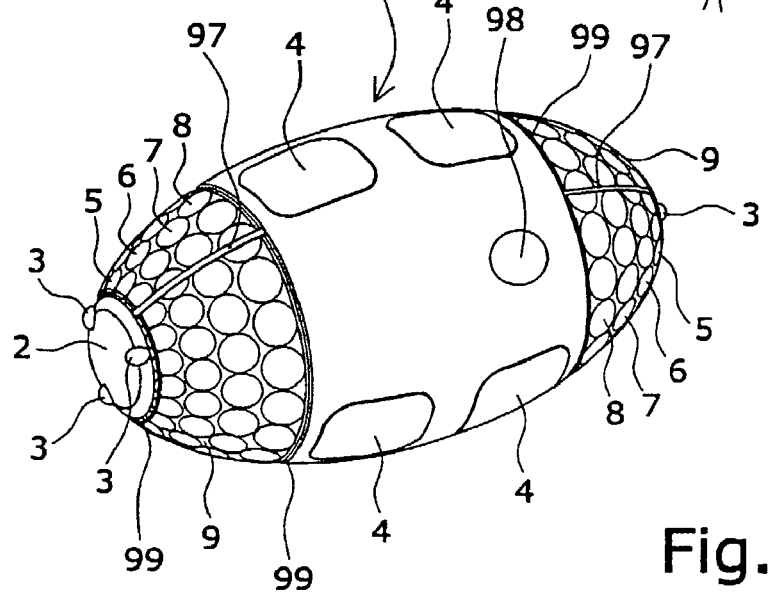
Fig. 1b

Fig. 3a
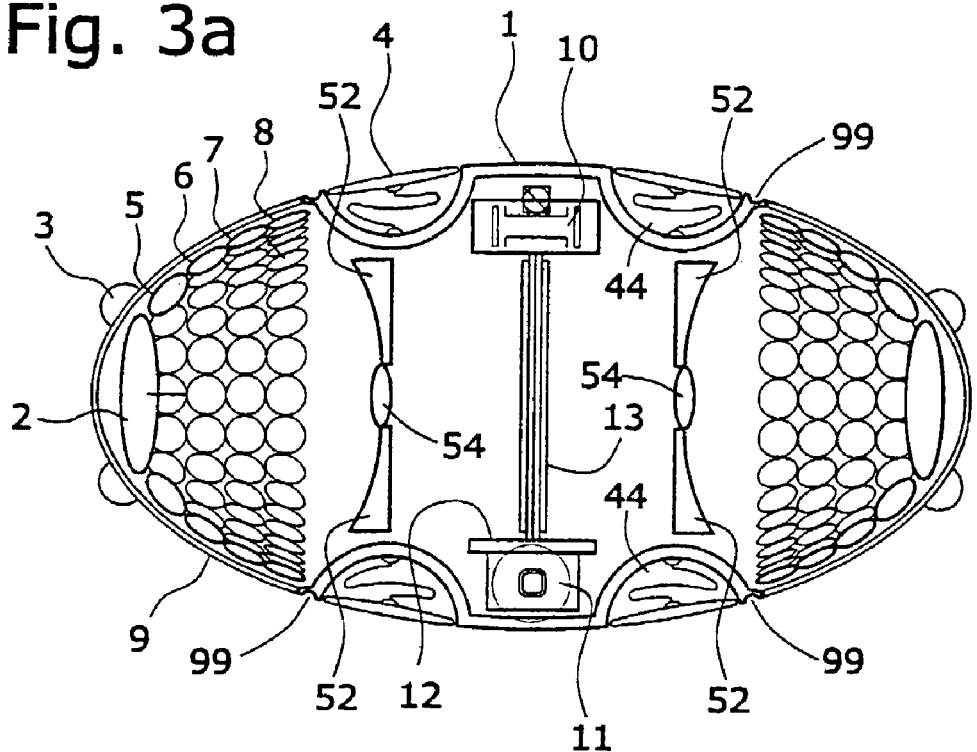
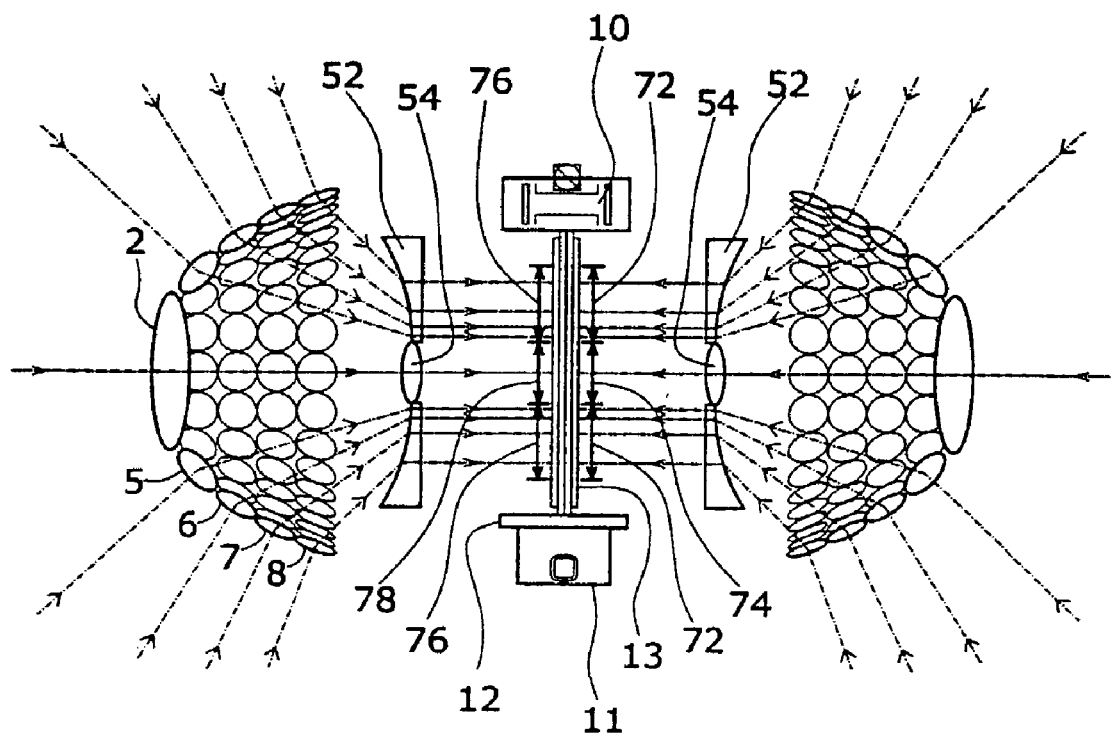
Fig. 3b

Fig. 4a
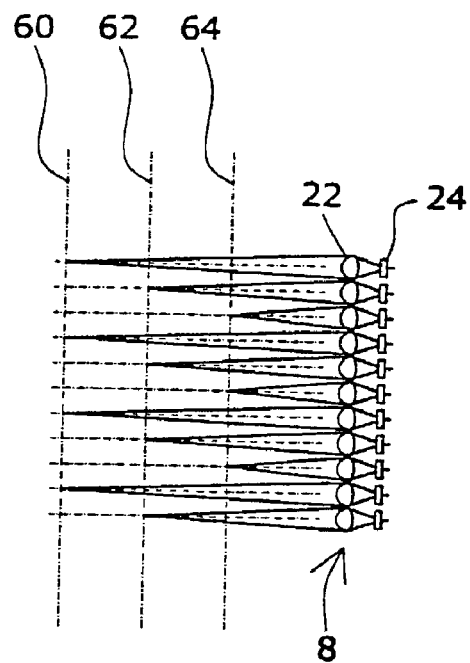
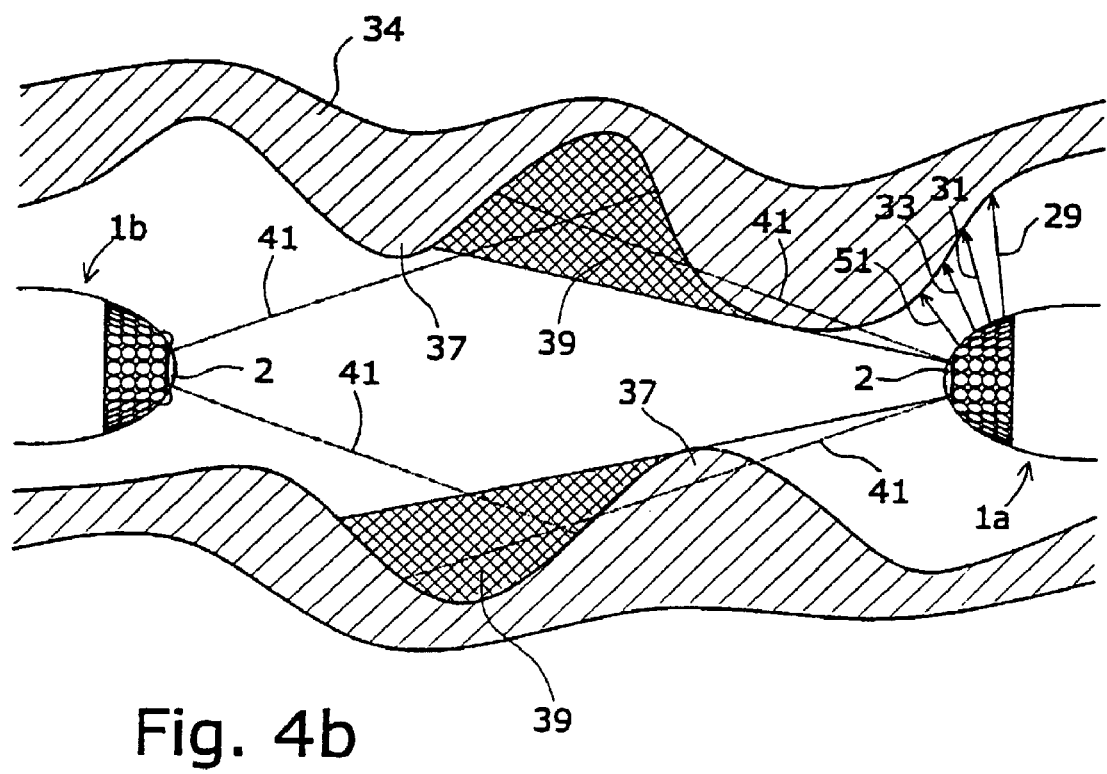
Fig. 4b

Fig. 5a
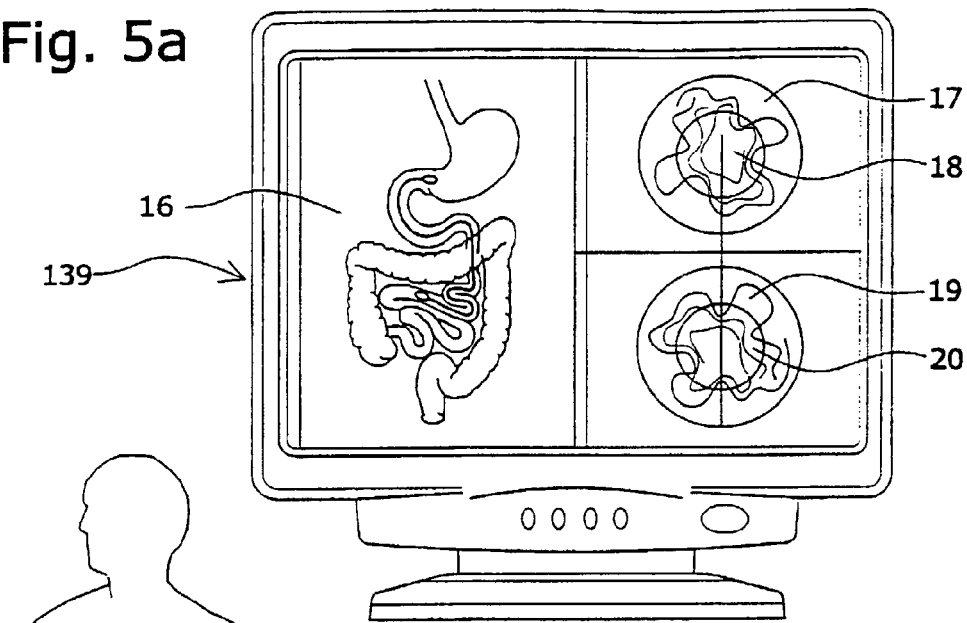
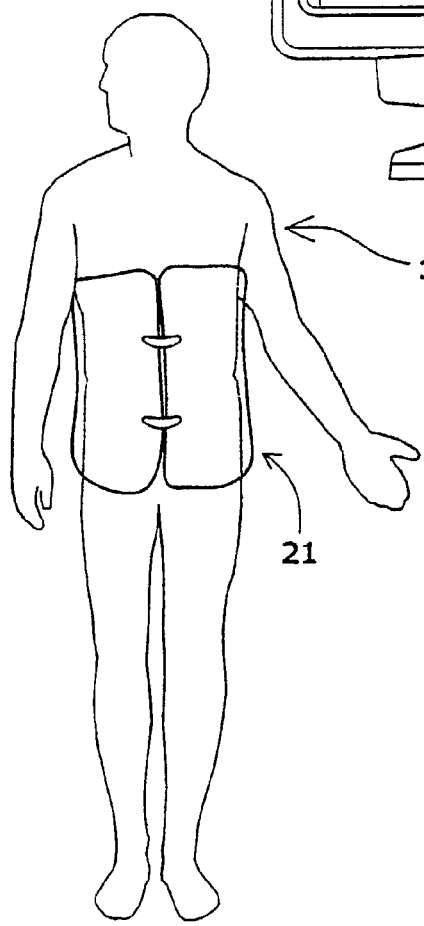
Fig. 5b
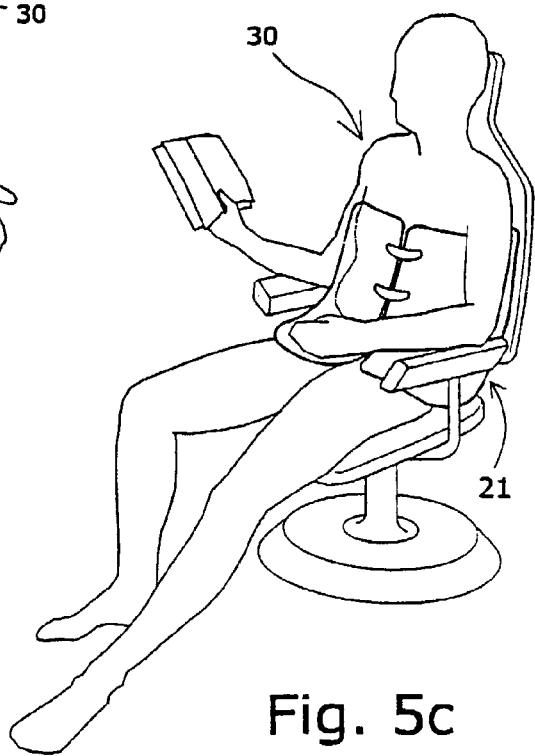
Fig. 5c

ENCAPSULATED MEDICAL IMAGING DEVICE AND METHOD

FIELD OF THE INVENTION

The present invention relates to medical imaging. More particularly it relates to an encapsulated medical imaging device and method for imaging gastro intestinal tract in patients, using scanning technologies.

BACKGROUND OF THE INVENTION

The gastrointestinal tract in adult humans is about 7-9 meters in total. Presently, of these 7-9 meters only as much as about 1.2 meters, extending from the ends of the gastrointestinal (GI) tract inwardly, may be imaged in commonly practiced medical imaging techniques (colonoscopy). Usually such imaging techniques involve inserting a tubular optical device (such as fiber optics) into the upper digestive system through the mouth (gastroscopy) or into the colon through the anus (colonoscopy) and advancing it along the gastrointestinal tract to inspect it and detect the presence of pathologies.

It may take years for a colon polyp to grow and turn malignant. In the absence of neurological warning system to indicate the occurrence of malignancies in their early stages it is often that the diagnosis of gastrointestinal malignancies is too late to be cured. Problems in the GI tract are ever too often detected only when they appear in great gravity and even then detection is made possible through the discovery of secondary indications (such as fecal occult blood occurrence). Early detection can be a major factor in improving the patient's chances of survival.

Some of the commonly occurring GI diseases include GI internal bleeding, inflammations of the GI tract, polyps, tapering of the GI tract, intestinal perforation, arteriovenous malformation. Internal bleeding may be caused by ulcer or varicose veins. These diseases cannot be detected in X-ray imaging or other non-invasive imaging methods until they evolve to traumatic proportion, yet even when diagnosed it is difficult to point out their exact location if that happens to fall beyond the inspectable range.

GI tract cancers are considered major factor in older adults fatalities. Gastrointestinal malignancies are considered to be the $2^{nd}$ highest factor in male fatalities, and $3^{rd}$ highest factor in female fatalities. GI diseases may be classified with reference to their location in the GI tract and the distribution of these diseases was found to be as follows: 30 per cent occurring in the esophagus, stomach and duodenum, 10 per cent occurring in the small intestine and some 60 percent occurring in the large intestine.

The inability to image the small intestine may bring about the need to perform investigative abdomen incision, sometimes just for ruling out a vague suspicion of malignancy.

Although some 80 per cent of the GI diseases may supposedly be detected by colonoscopy or gastroscopy, sometimes these invasive techniques may be considered undesired. These techniques are relatively costly, requiring the presence of a several member medical team throughout the procedure. Furthermore it is statistically shown that about one in 2000 patients is prone to perforation of the GI tract caused by a sharp object (the imaging tool) during the performance of the procedure. Such an incident immediately requires surgical intervention.

U.S. Pat. No. 5,604,531 (Iddan et al.) entitled IN-VIVO VIDEO CAMERA SYSTEM, filed in 1995, and incorporated herein by reference, discloses an in-vivo video camera system and an autonomous video endoscope The system includes a swallable capsule, a transmitter and a reception system. The swallable capsule includes a camera system and an optical system for imaging an area of interest onto the camera system. The transmitter transmits the output of the video camera system and the reception system receives the transmitted video output.

U.S. Pat. No. 4,278,077 (Mitzumoto) entitled MEDICAL CAMERA SYSTEM, filed in 1979, and incorporated herein by reference, discloses a capsule-shaped miniature camera comprising at least one permanent magnet, an induction coil, a lamp serially connected to the induction coil and a shutter device. The induction coil induces an electromotive force when a magnetic field generated by electromagnets outside the camera acts on it. The electromotive force turns on the lamp and drives the shutter device.

The video camera system of the '531 patent (Iddan) employs analog video and analog transmission. It is evident that it provides an image focused at a predetermined fixed distance from the optical lens and consequently, due to the poor lighting conditions within the GI tract, blurred image of objects falling outside or falling short of the focal range. As the GI tract is composed of parts of different diameters (the esophagus, stomach, small and large intestines) it is anticipated that substantial information will be omitted or severely degraded in the image obtained by Iddan's system. Furthermore the inside walls of the GI tract are also present "hilly" topography, and therefore pose difficulties to the imaging abilities of that system.

It is noted that these prior art optical imaging devices are limited in their field of view as they include a single optical system and are therefore limited to one directional view. For irregular surfaces as exist in the GI tract this may result in many hidden areas that the imager will not view properly. Furthermore the possibility of the capsule flopping over or turning around is real and may hamper with the proper functionality of the device.

BRIEF DESCRIPTION OF THE INVENTION

It is therefore thus provided, in accordance with a preferred embodiment of the present invention, an encapsulated medical imaging system comprising:
  a capsule of swallowable proportion comprising:
    at least one optical setup of a number of optical setups comprising an array of microlenses distributed in axial symmetry on at least a portion of the capsule so that the array of microlenses is capable of receiving light reflected from object located in at least a sector outside the capsule;
    corresponding optical array comprising an array of light sensitive cells optically communicating with said optical setup through focusing means, such that the image of the object is focused on the array of light sensitive cells;
    electronic circuitry adapted to sample image data obtained by the optical array by scanning the image and converting the image data to digital data;
    illuminating means for illuminating a sector in front the optical setup, outside the capsule;
    transmitting means communicating with said electronic circuitry, adapted to receive image digital data and transmit it to an external receiver;
  receiving means for receiving data transmitted from said capsule;
  image processing means for processing the data received by the receiving means and; and
  display means for displaying an image.

Furthermore, in accordance with another preferred embodiment of the present invention, the number of the optical setups comprises two optical setups, arranged in opposite sides of the capsule, so as to allow counter-directional viewing.

Furthermore, in accordance with another preferred embodiment of the present invention, the capsule is provided with at least one lens of a number of lenses for central view and wherein the array of microlenses is arranged in a coronal arrangement with respect to the lens, so as to provide peripheral view.

Furthermore, in accordance with another preferred embodiment of the present invention, the number of lenses comprises two lenses.

Furthermore, in accordance with another preferred embodiment of the present invention, the microlens array comprises a plurality of microlenses having different foci distributed in a known distribution, and wherein the processing means is adapted to identify and distinguish focused image data from unfocused one, disregard the unfocused data and acquire image made of focused data only.

Furthermore, in accordance with another preferred embodiment of the present invention, the illumination means comprises light emitting diodes.

Furthermore, in accordance with another preferred embodiment of the present invention, the light emitting diodes illuminate light in different frequency ranges.

Furthermore, in accordance with another preferred embodiment of the present invention, the light emitting diodes emit red, green or blue light.

Furthermore, in accordance with another preferred embodiment of the present invention, the light emitting diodes are operated so as to sequentially illuminate red green and blue light. Furthermore, in accordance with another preferred embodiment of the present invention, the capsule is about 12-20 mm in length and about 5-7 mm in diameter.

Furthermore, in accordance with another preferred embodiment of the present invention, the capsule housing is made from a biocompatible material.

Furthermore, in accordance with another preferred embodiment of the present invention, the capsule housing is made from a dissolvable material.

Furthermore, in accordance with another preferred embodiment of the present invention, the capsule housing is made from a dissolvable material that is durable enough so that it may pass an entire GI tract without disintegrating during the estimated period of time it would normally take for the capsule to pass through.

Furthermore, in accordance with another preferred embodiment of the present invention, the capsule is internally powered.

Furthermore, in accordance with another preferred embodiment of the present invention, the capsule is externally powered.

Furthermore, in accordance with another preferred embodiment of the present invention, the capsule is inductively powered.

Furthermore, in accordance with another preferred embodiment of the present invention, the capsule is further provided with supporting means for supporting the capsule and preventing its turning over or around.

Furthermore, in accordance with another preferred embodiment of the present invention, said supporting means comprise extractable surfaces.

Furthermore, in accordance with another preferred embodiment of the present invention, the extractable surfaces are supported by arms.

Furthermore, in accordance with another preferred embodiment of the present invention, said arms are resilient.

Furthermore, in accordance with another preferred embodiment of the present invention, said arms are mechanically foldable.

Furthermore, in accordance with another preferred embodiment of the present invention, the arms are adapted to be housed in cavities provided in the housing of the capsule.

Furthermore, in accordance with another preferred embodiment of the present invention, the cavities are adapted to hold samples obtained by the arms.

Furthermore, in accordance with another preferred embodiment of the present invention, the capsule is further provided with a medical parameter sensor.

Furthermore, in accordance with another preferred embodiment of the present invention, the sensor comprises a temperature sensor or a pressure sensor.

Furthermore, in accordance with another preferred embodiment of the present invention, the capsule is further provided with wiping means for wiping dirt off the optical setup.

Furthermore, in accordance with another preferred embodiment of the present invention, the wiping means comprises a wiping arm.

Finally, in accordance with another preferred embodiment of the present invention, there is provided an encapsulated medical imaging system comprising:

a capsule of swallowable proportion comprising:
  at least one optical setup of a number of optical setups comprising an array of multi-focal lenses distributed in axial symmetry on at least a portion of the capsule so that the array of multi-focal lenses is capable of receiving light reflected from object located in at least a sector outside the capsule;
  corresponding optical array comprising an array of light sensitive cells optically communicating with said optical setup through focusing means, such that the image of the object is focused on the array of light sensitive cells;
  electronic circuitry adapted to sample image data obtained by the optical array by scanning the image and converting the image data to digital data;
  illuminating means for illuminating a sector in front the optical setup, outside the capsule;
  transmitting means communicating with said electronic circuitry, adapted to receive image digital data and transmit it to an external receiver;
receiving means for receiving data transmitted from said capsule;
image processing means for processing the data received by the receiving means and; and
display means for displaying an image.

BRIEF DESCRIPTION OF THE FIGURES

In order to better understand the present invention, and appreciate its practical applications, the following Figures are provided and referenced hereafter. It should be noted that the Figures are given as examples only and in no way limit the scope of the invention as defined in the appending claims. Like components are denoted by like reference numerals.

FIG. 1a illustrates a patient's GI tract with an encapsulated medical imaging device in accordance with the present invention traveling through it.

FIG. 1b illustrates a general view of an encapsulated medical imaging device in accordance with a preferred embodiment of the present invention.

FIG. 3a is a see-through view of a preferred embodiment of the encapsulated medical imaging device of the present invention.

FIG. 3b depicts the optical scheme of the device of FIG. 3a.

FIG. 4a illustrates a single stretched row of the microlens array of the device of FIG. 3a.

FIG. 4b, illustrates fields of view of an encapsulated medical imaging device in accordance to the present invention as it travels through an intestine.

FIGS. 5a, 5b and 5c illustrate a display monitor communicating with a receiving unit of an encapsulated medical imaging device of the present invention incorporated in a vest worn by a patient.

DETAILED DESCRIPTION OF THE INVENTION AND FIGURES

Figure 2A:
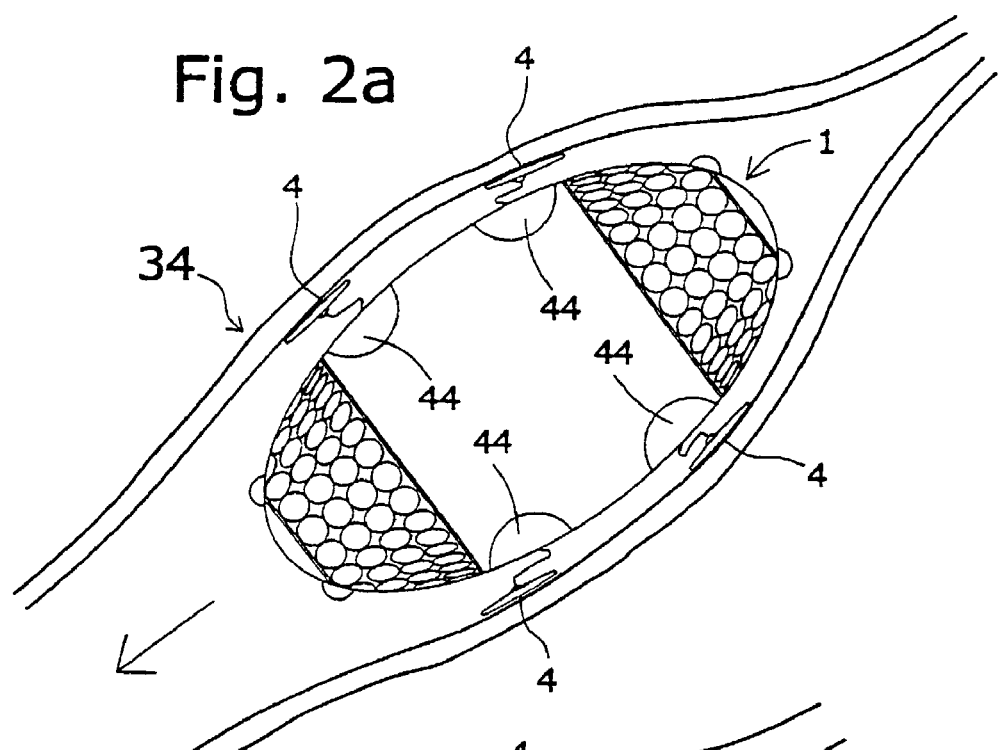
FIG. 2a illustrates the encapsulated medical imaging device of the present invention provided with arms, shown in semi-retracted state as it travels through a small intestine.

A main aspect of the present invention is the provision of a multi-focal hemispherical-like array, capable of capturing focused images of various portions of the inspected objects located at different distances from the capsule.

Another main aspect of the present invention is the provision of optical array and the performance of scanning of the object rather than simply taking pictures frame-by frame. The resolution of the image is determined by the number of pixels, which corresponds to the number of photosensors of a optical array utilized in the present invention. Scanning allows greater resolution to be attained in comparison with video imaging (as suggested in Iddan's '531 patent), obtaining segment-by-segment image of the viewed object.

The structure and mode of operation of the encapsulated medical imaging device of the present invention is herein explained with reference to the accompanying Figures.

Reference is made to FIG. 1a, illustrating a patient's GI tract with an encapsulated medical imaging device in accordance with the present invention traveling through it. Initially the patient 30 is made to swallow the capsule 1. Capsule 1, having dimensions suitable for it to be taken orally and swallowed, after having been swallowed, immediately starts transmitting image data. It is traveling through the patient's GI tract 35, the GI tract generally comprising the esophagus 38, stomach 32, small intestine 34 and large intestine 36. The capsule is shown located at the small intestine 34 of the patient, traveling through it and transmitting information as it travels through. Typical anticipated dimensions for the capsule would be approximately 12-20 mm in length and about 5-7 mm in diameter. The capsule housing is made of biocompatible non-toxic matter.

The encapsulated medical imaging device generally includes optical system, illumination system, optical array for obtaining digital representation of the image obtained by the optical system, electronic circuitry, and transmitting means. The electronic circuitry is externally powered or it may contain an internal power source.

The capsule advances through the GI tract due to the normal intestinal action (contraction and relaxation of the GI tract muscular tissue). Due to its small size the capsule leaves the body with the excrement anally.

In a preferred embodiment of the present invention the housing of the capsule is made of dissolvable material (such as the material used for producing medication capsules), so that in the event of pathological narrowing of the intestines the capsule will not be stuck there. Naturally such material should be made durable enough so that it may pass the entire GI tract without disintegrating during the estimated period of time it would normally take for the capsule to pass through.

As it may be possible for the capsule to roll over and turn around when it advances through the GI tract the capsule is provided with dual optics so that in fact it includes two viewing means oppositely directed. This feature is also important when the view of the front viewing optics is locally obstructed by a protrusion on the surface rising from the intestine wall (like a polyp).

The system is supplemented by external receiving unit for receiving the data transmitted from the capsule, and a control unit for processing said data and displaying the images obtained.

FIG. 1b illustrates a general view of an encapsulated medical imaging device in accordance with a preferred embodiment of the present invention. The capsule 1, in this example having a housing 40 of elongated dimensions, comprises two optical setups, each having an axial hemispherical symmetry and located at either ends of the capsule. The capsule housing 40 is provided with arms 42 having flat feet 4 substantially covering cavities 44 in which the foldable arms are housed (see also FIGS. 2a and 2b and the corresponding description in this specification for the use and operation of these arms). Each end of the capsule is provided with a front lens 2, for viewing objects in front of that end, light emitting diodes (LED) 3 for illuminating a sector in close proximity of the capsule (at least covering the whole range of the optical focused field of view of the optical components of the device), and an array of microlenses 9 made up of a multiple rows of microlenses (depicted in these Figures, for the sake of simplicity, are only four rows 5, 6, 7, and 8, but in reality a much larger number of rows of microlenses is employed). The optical set-up is described in detail with reference to FIGS. 3a, 3b, 4a and 4b). For example, microlens arrays are commercially available from MEMS Optical Inc (Huntsville, Ala., USA).

The LED diodes 3 may optionally be sources of light in different frequencies, for example omitting light in the RGB ranges (i.e. one omitting red, another omitting green and, yet another omitting blue light). This is to allow scanning in different monochromatic illumination by turning on separately and sequentially each LED color and then combining the different mono-chromatic gray-scale images into one color image by the processing means of the system.

An optional wiper 97 is provided comprising a wiping arm traveling over the microlens array, bound by tracks 99, so as to cover the entire microlens array, and wipe dirt off the lenses.

Further optional feature is a sensor 98 for sensing medical parameters such as local temperature, pressure or other parameters that communicates with the electronic control of the capsule and thus capable of transmitting the sensed data to an external receiver.

FIG. 2a illustrates the encapsulated medical imaging device of the present invention provided with arms, shown in semi-retracted state as it travels through a small intestine. The arms 42 of the device are provided so as to provide support for the device against the intestine wall 34 as the arms' feet 4 lean against the wall, and prevent the device from flopping over or turning sideways. The arms may be resilient or mechanically foldable and deployable so as to apply slight counter-force onto the intestine wall and enhance its supporting ability. The arms may alternatively of complementarily be sampling means, for sampling tissue or matter from the intestine wall. In the latter case, the arms are each adapted to be operated separately (via controlling means) and adapted to be able to be retracted into its corresponding cavity 44 so as to keep the sample inside the cavity once it is retrieved.

Figure 2B:
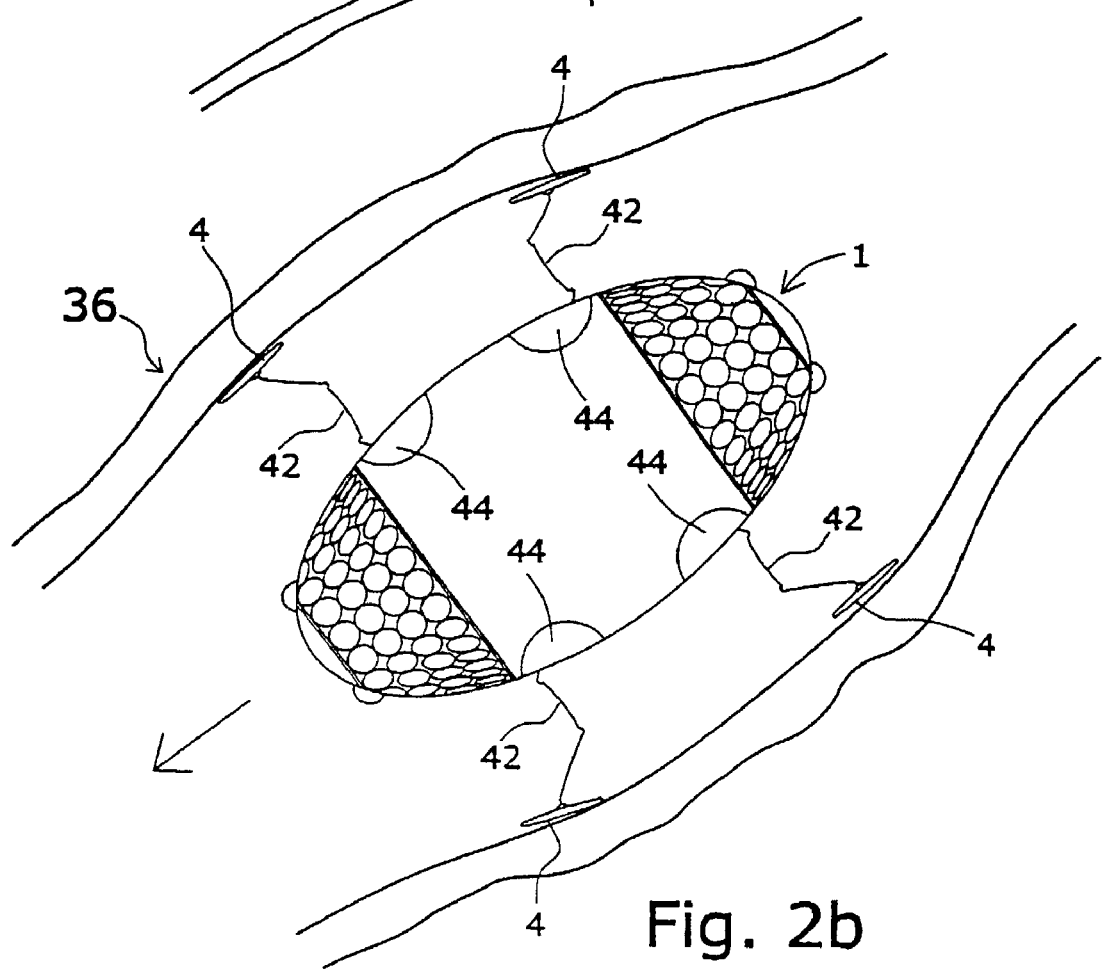
FIG. 2b depicts the encapsulated medical imaging device of FIG. 2a with its arms fully deployed as it travels through a large intestine.

FIG. 2b depicts the encapsulated medical imaging device of FIG. 2a with its support arms deployed as it travels through a large intestine. As the large intestine 36 is wider the arms may employ fully and reach to the intestine wall so as to prevent disorientation of the capsule.

In another preferred embodiment of the present invention, feet 4 may be as large as the entire housing, or substantial portions of it, thus providing larger contact surface with the intestinal wall.

FIG. 3a is a see-through view of a preferred embodiment of the encapsulated medical imaging device of the present invention. Microlens array 9 focuses light reflected form image outside the capsule. It is noted that each microlens may see different view, as some face certain sector and others face other sectors. An optical array is provided inside the capsule, typically comprising an array of light-sensitive receiving cells 12. As the embodiment shown in the figures has twin optical set-up, aimed at providing two counter-directional viewing ability, two optical arrays are provided, positioned back to back so that each faces one end of the device, located in the focal plane of the corresponding optical set-up. The complete image imprinted on the optical array is a result of aggregation of images obtained by each microlens. The optical array is sampled for data by corresponding electronic circuitry 11, which samples in a predetermined manner rows or columns or any other predetermined arrangement, and convert the analog data to digital data. The device is in fact scanning the image in scanning technology.

Optionally it may be required to place appropriate correction optical lenses 52, 54 between each optical array and its corresponding optical set-up. Electronic control units 10, 11 are each electrically communicating with the optical arrays, as well as controlling the light diodes 3, and powering them. The control unit is adapted to generate transmission of data obtained by the optical array to an external receiver.

It is possible to provide the device with internal power source, such as a battery, or provide inductive circuitry (see for example U.S. Pat. No. 4,278,077 to Mitzumoto) that is powered by induction from an external inductive source.

FIG. 3b depicts the optical scheme of the device of FIG. 3a. Each microlens of microlens array 9 views a small sector of the hemispherical surroundings of the device, and is focused via the optical lenses to an appropriate corresponding cell of the optical array. Front and back images are focused through the front and back lenses 2 onto central area 78 of the optical array, whereas the peripheral image obtained by coronal microlens array 9 is focused onto an outer annular strip portion 76. Identically, the image obtained by the optics of the other end of the capsule is focused on central area 74 and peripheral area 72 of the optical array.

It is stipulated that if the curvature of the microlens array 9 corresponds to the curvature of the front lens 2, than a continuous image of the objects viewed outside the capsule may be obtained. Alternatively two separate images may be displayed on an external monitor—one of the view from the front lens and one of the peripheral view viewed by the microlens array. A combined image may also be constructed. In a preferred embodiment of the present invention, all image manipulation is carried out by an external processing unit (as described hereafter).

FIG. 4a illustrates a single stretched row of the microlens array of the device of FIG. 3a. In a preferred embodiment of the present invention the microlens array comprises a plurality of microlenses 22, arranged in a sequential manner with lenses having different focal distance distributed in that row. The different foci lenses are arranged so that for a particular angle of view there exist all types of the various microlens lens, and each lens is focused on a corresponding cell of the light receiving array of cells (such as photoelectric cells). A first group of lenses is focused on an imaginary plane 60 located at a first predetermined distance from the array. A second group of lenses is focused on an imaginary plane 62 located at a second predetermined distance from the array, closer than plane 60. A third group of lenses is focused on an imaginary plane 64 located at a third predetermined distance from the array closer still. This way the microlens array has three focus planes and not only one.

The virtue of this feature can be appreciated by referring to FIG. 4b, illustrating fields of view of an encapsulated medical imaging device in accordance to the present invention as it travels through an intestine.

As the capsule arrives (position 1a) some portions of the intestine walls 39 are hidden as a protrusion 37 blocks its field of view. In fact the inside walls of the intestine are very irregular. Chyme (mixed food and digestive juices) is pushed through the small intestine through muscular contractions. During these contractions the chyme, having the consistency of runny applesauce, is squished into the lining of the wall of the small intestine. Nutrients are absorbed via osmosis by the blood vessels in the mesentery and absorbed through osmosis by the blood vessels attached to the outside of the small intestine. The lining of the intestine is hilly so as to present large surface area for that osmosis to take place. However when the capsule crosses over to position 1b its rear optics allows viewing that hidden area and thus the limitations of the prior art devices concerning their field of view is greatly reduced.

It is clearly seen that the capsule may be positioned in different distances 31, 33, 29, 51) from the intestine wall lining. If an inspected object is located at a certain distance 31 that equals to the focal distance of one of the microlens groups, than its best available image will be acquired from that lens (in fact from a plurality of close lenses from that same group). The control unit of the device or the external monitoring means which receive the transmission is preferably provided with image processing software adapted to identify only focused images and disregard blurred images obtained from the other lens groups. Thus the device is capable of providing clear and focused images of objects at various distances from the device. The processing unit is thus adapted to identify and distinguish focused image data from unfocused one, disregard the unfocused data and acquire image made of focused data only.

Similarly, in another preferred embodiment of the present invention, an alternative optical setup may include multiple multi-focal lenses.

FIGS. 5a, 5b and 5c illustrate a display monitor communicating with a receiving unit of an encapsulated medical imaging device of the present invention incorporated in a vest 21 worn by a patient. Vest 21 houses the receiving unit adapted to communicate with the capsule and may also include powering means such as inductive circuitry. It engulfs the patients' torso effectively close to the capsule as it travels through the patient's GI tract. The receiving unit in the vest communicates via cable or wirelessly with monitoring unit 139. Monitoring unit 139 provided with display means for displaying one or several images 17, 18, by the encapsulated medical imaging device and/or other data 16.

Figure 6:
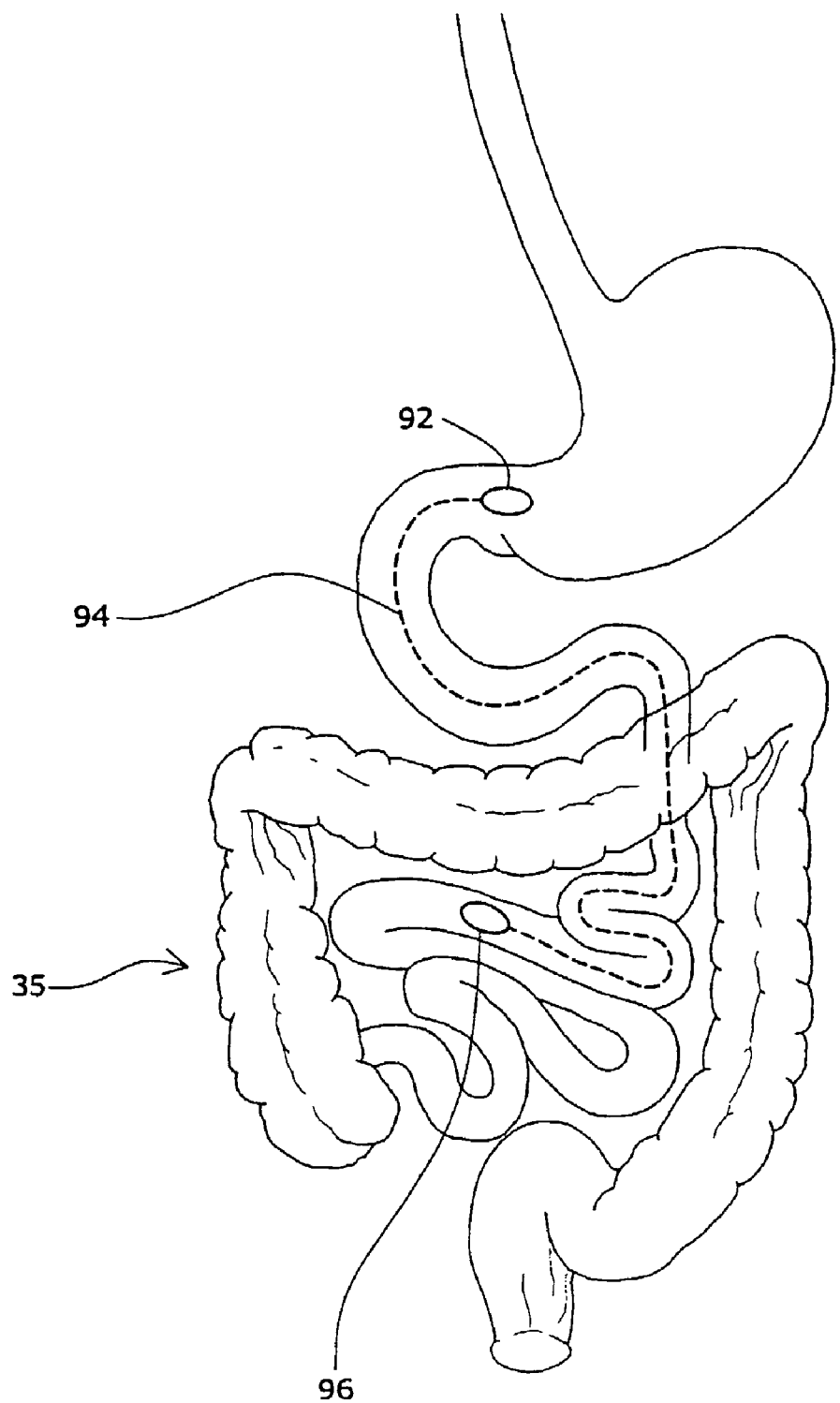
FIG. 6 illustrates a way to calculate the correct position of a suspected pathology detected by the encapsulated medical imaging device of the present invention.

FIG. 6 illustrates the path traveled by a capsule in a patient's small intestine. In another preferred embodiment of the present invention the device incorporates with monitoring means adapted to identify the position and location within the GI tract where an image was acquired by comparing it to a prearranged library of images, and identifying by image processing the type of environment the capsule was in when the image was acquired. It is stipulated that each portion of the GI track (i.e. esophagus, small intestine, large intestine stomach) has unique image (texture, shape, and other distinct features). By identifying the type of environment the device was in when the image was acquired and by knowing some parameters such as the sampling rate of the device, its traveling velocity within the GI tract (on average it is assumed that it would travel at the rate of 1 to 3 cm per second) it is possible to determine or at least estimate the distance of the path 94 traveled by the capsule from the last identified position 92 to the current location 96, where a pathology was detected and viewed by the capsule. The software may generate a general view of the GI tract, the last image obtained as the device entered into the current type of GI tract and most recent image obtained. A graphic indication on the general image, in the form of a cursor, arrow or any other graphical representation, may be superposed on the GI tract image indicating the device current (or recent) location. This can substantially enhance the medical team's ability to locate the exact position of the pathology found in position 96.

Figure 7:
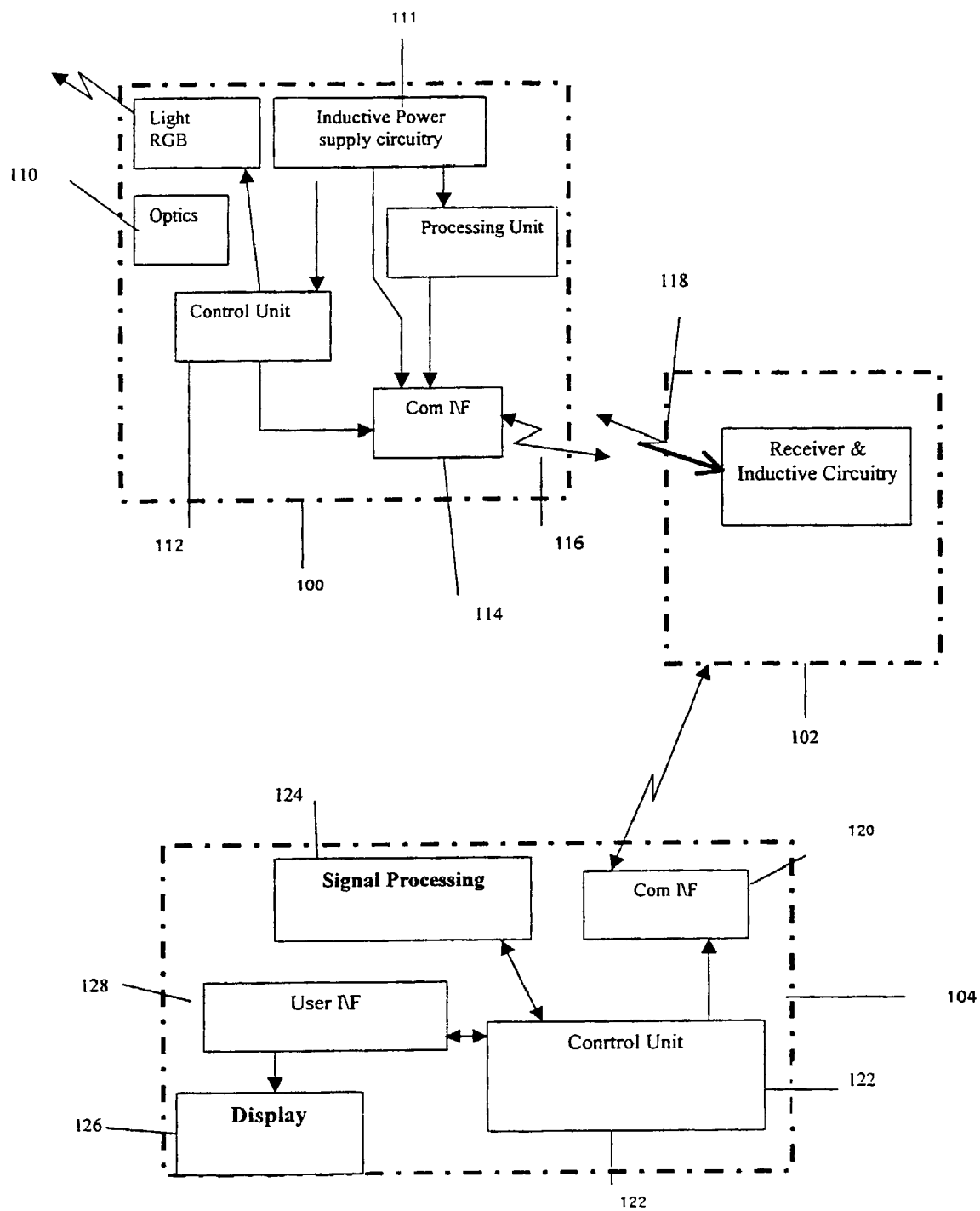
FIG. 7 illustrates an optional schematic configuration of the electronic system of an encapsulated medical imaging device in accordance with a preferred embodiment of the present invention.

FIG. 7 illustrates an optional schematic configuration of the electronic system of an encapsulated medical imaging device in accordance with a preferred embodiment of the present invention. This is given as an example only. A person skilled in the art could easily provide other electrical configurations that would still be covered by the scope of the present invention.

The capsule 100 generally comprises optics 110 (the lenses and optical array) communicating with a control unit 112 that transmits the digital data obtained from the optical array via communication interface 114 and antenna 116. The capsule is optionally inductively powered by an inductive circuitry 111 energized externally by inductance. A receiver 102 (such as one incorporated in a vest—see FIGS. 5b and 5c) picks up the data transmitted by an antenna 118 and communicates with a control unit 104. The control unit comprises communication interface 120, control unit 122, processor 124, and display means 126 (such as a monitor). It is optionally also provided with a user interface 128, for inputting commands to the control unit. In a preferred embodiment of the present invention the control unit is programmed or programmable so that physician can adjust the sampling rate of the device (i.e. the frequency of image acquiring), control the foldable arms, choose the images to be displayed or command the system to perform calculations (such as the distance traveled by the capsule inside the intestine).

The advantages of the encapsulated imaging device of the present invention are numerous. The device provides high accessibility to the entire GI tract. The unique optical setup provides better images and a greater range for focused images. Optional sampling arms may be operated in-vivo and obtain samples such as biopsy, blood test or retrieve any other sample from the matter the device comes near to. External energizing prevents the need for internal power source that may be hazardous to the patient if the capsule disintegrates within the GI tract.

In a preferred embodiment of the present invention the images may be obtained by scanning in RGB light—first scanning in red light, then scanning in green and finally in blue, each time obtaining mono-chromatic gray-scale quality images and incorporating them into a color image by the processing means of the external unit and presenting the color image on the monitor.

Note that the system described in the specification and figures is mainly designed to obtain black and white images, but these images are remarkably clear and distinct and the anticipated resolution is much greater than that of video images.

It should be clear that the description of the embodiments and attached Figures set forth in this specification serves only for a better understanding of the invention, without limiting its scope as covered by the following claims.

It should also be clear that a person skilled in the art, after reading the present specification could make adjustments or amendments to the attached Figures and above described embodiments that would still be covered by the following claims.

The invention claimed is:

1. A medical imaging system comprising:
an elongated capsule comprising:
a housing of swallowable proportions and having a longitudinal axis with a first end and an oppositely positioned second end, comprising:
two optical setups, a first optical setup positioned on the longitudinal axis at or near the first end and a second optical setup positioned on the longitudinal axis at or near the second end, for viewing sectors external to the housing and in opposite directions;
at least one illuminator illuminating said sectors;
at least one light sensitive array receiving light from one of the optical setups and generating image data;
electronic circuitry for sampling image data from said light sensitive arrays and converting image data to digital data; and
a transmitter receiving said digital data and transmitting said digital data,
an external receiver receiving said digital data from said transmitter;
an image processor capable of processing said digital data received by said external receiver into at least one image; and
a display capable of displaying said at least one image.

2. The medical imaging system as claimed in claim 1, further comprising a coronal array of microlenses distributed coronally to at least one of the optical setups focusing light on a light sensitive array.

3. The medical imaging system as claimed in claim 2, wherein microlenses of said microlenses array have different foci distributed in a known distribution and wherein said image processor is capable of distinguishing focused image data from unfocused image data and disregarding at least a portion of said unfocused data.

4. The medical imaging system as claimed in claim 1, wherein said at least one illuminator comprises light emitting diodes.

5. The medical imaging system as claimed in claim 4, wherein said light emitting diodes emit light in different frequencies.

6. The medical imaging system as claimed in claim 5, wherein said light emitting diodes emit red, green, and blue light.

7. The medical imaging system as claimed in claim 1, wherein said longitudinal axis is from about 12 to 20 mm in length and said capsule housing has a diameter of from about 5 to 7 mm.

8. The medical imaging system as claimed in claim 1, wherein said capsule housing is made of biocompatible material.

9. The medical imaging system as claimed in claim 1, wherein said capsule housing comprises disposable material.

10. The medical imaging system as claimed in claim 9, wherein said capsule housing comprises dissolvable material sufficiently stable to pass through a patient's entire gastrointestinal tract without disintegrating.

11. The medical imaging system as claimed in claim 1, wherein said capsule is internally powered.

12. The medical imaging system as claimed in claim 1, wherein said capsule is externally powered.

13. The medical imaging system as claimed in claim 12, wherein said capsule is inductively powered.

14. The medical imaging system as claimed in claim 1, wherein said capsule is further provided with stabilizing support for supporting the capsule in preventing it from turning over and around.

15. The medical imaging system as claimed in claim 14, wherein said support comprises one or more retractable surfaces.

16. The medical imaging system as claimed in claim 15, wherein said retractable surfaces are supported by arms.

17. The medical imaging system as claimed in claim 16, wherein said arms are resilient.

18. The medical imaging system as claimed in claim 16, wherein said arms are mechanically foldable.

19. The medical imaging system as claimed in claim 16, wherein said arms are capable of being housed in cavities provided in said capsule housing.

20. The medical imaging system as claimed in claim 19, wherein said cavities are capable of holding samples obtained by said arms.

21. The medical imaging system as claimed in claim 1, wherein said capsule housing is further provided with a medical parameter sensor.

22. The medical imaging system as claimed in claim 21, wherein said sensor is a temperature sensor or a pressure sensor.

23. The medical imaging system as claimed in claim 1, wherein said capsule housing is further provided with at least one wiper for wiping off an outer surface of at least one of said optical lens arrays.

24. The medical imaging system as claimed in claim 23, wherein said wiper comprises a wiping arm.

25. The medical imaging system as claimed in claim 1, wherein the longitudinal axis is fixed and linear.

26. The medical imaging system as claimed in claim 1, wherein the optical setups are lens arrays.

27. An elongated capsule for imaging a patient's gastrointestinal tract, comprising:
a housing of swallowable proportions and having a longitudinal axis with a first end and an oppositely positioned second end,
two optical setups, a first optical setup positioned on the longitudinal axis at or near the first end and a second optical setup positioned on the longitudinal axis at or near the second end, for viewing sectors external to the housing and in opposite directions;
at least one illuminator illuminating said sectors;
two light sensitive arrays, each receiving light from one of the corresponding optical setups and generating image data;
electronic circuitry for sampling image data from said light sensitive arrays and converting image data to digital data; and
a transmitter for transmitting said digital data.

28. The elongated capsule as claimed in claim 27 which further comprises a coronal array of microlenses distributed coronally to at least one of the optical setups focusing light on a light sensitive array.

29. The elongated capsule as claimed in claim 28, wherein microlenses of said microlenses array have different foci distributed in a known distribution.

30. The elongated capsule as claimed in claim 27, wherein said at least one illuminator comprises light emitting diodes.

31. The elongated capsule as claimed in claim 30, wherein said light emitting diodes emit light in different frequencies.

32. The elongated capsule as claimed in claim 27, wherein said longitudinal axis is from about 12 to 20 mm in length and said capsule housing has a diameter of from about 5 to 7 mm.

33. The elongated capsule as claimed in claim 27, wherein the capsule housing comprises dissolvable material sufficiently stable to pass through the patient's entire gastrointestinal tract without disintegrating.

34. The elongated capsule as claimed in claim 27, wherein the capsule is internally powered.

35. The elongated capsule as claimed in claim 27, wherein the capsule is externally powered.

36. The elongated capsule as claimed in claim 35, wherein said capsule is inductively powered.

37. The elongated capsule as claimed claim 27, wherein the capsule is further provided with stabilizing support for supporting the capsule in preventing it from turning over and around.

38. The elongated capsule as claimed in claim 37, wherein said support comprises one or more retractable surfaces.

39. The elongated capsule as claimed in claim 38, wherein said retractable surfaces are supported by arms.

40. The elongated capsule as claimed in claim 39, wherein the arms are resilient.

41. The elongated capsule as claimed in claim 39, wherein the arms are mechanically foldable.

42. The elongated capsule as claimed in claim 39, wherein cavities are provided in the capsule housing and the arms are capable of being housed in the cavities.

43. The elongated capsule as claimed in claim 42, wherein the cavities are capable of holding samples obtained by said arms.

44. The elongated capsule as claimed in claim 27, wherein the capsule housing is further provided with a medical parameter sensor.

45. The elongated capsule as claimed in claim 44, wherein said sensor is a temperature sensor or a pressure sensor.

46. The elongated capsule as claimed in claim 27, wherein the capsule housing is further provided with at least one wiper for wiping off an outer surface of at least one of said optical lens arrays.

47. The elongated capsule as claimed in claim 46, wherein the wiper comprises a wiping arm.

48. The elongated capsule as claimed in claim 27, wherein the longitudinal axis is fixed and linear.

49. The elongated capsule as claimed in claim 27, wherein the optical setups are lens arrays.

50. A method for imaging a patient's gastrointestinal tract, including imaging folds in the surface of the gastrointestinal tract, which comprises:

providing an elongated capsule of claim 27;
   inducing the patient to swallow the capsule;
   simultaneously acquiring data from the gastrointestinal tract as well as the folds by both optical setups; and
   processing information generated by electronic circuitry in the capsule to produce useful imagery.

51. The method of claim 50, wherein imagery obtained from a forward-looking lens optical array when the capsule is positioned at a first position in the patient's gastrointestinal tract is combined with imagery from a rearward-looking lens optical array when the capsule is at a second position distal to the first position, to provide a substantially complete image of the patient's gastrointestinal tract between the first position and the second position.

* * * * *